United States Patent [19]

Johnston et al.

[11] 4,180,395
[45] Dec. 25, 1979

[54] 6-FLUORO-3,5-DIHALO-2-PYRIDYLOXY COMPOUNDS

[75] Inventors: Howard Johnston, Walnut Creek, Calif.; Herman O. Senkbeil, Midland, Mich.

[73] Assignee: The Dow Chemical Company, Midland, Mich.

[21] Appl. No.: 786,702

[22] Filed: Apr. 11, 1977

Related U.S. Application Data

[63] Continuation-in-part of Ser. No. 765,190, Feb. 3, 1977, abandoned, which is a continuation of Ser. No. 568,339, Apr. 15, 1975, abandoned, which is a continuation-in-part of Ser. No. 460,010, Apr. 11, 1974, abandoned.

[51] Int. Cl.$^2$ .................. A01N 9/22; C07D 213/89
[52] U.S. Cl. ................................ 71/94; 546/5; 546/291; 546/302
[58] Field of Search ............ 260/295 R, 270 E, 295 S, 260/295 AM, 295 CA, 297 R; 71/94, 113; 424/263; 546/291, 302

[56] References Cited

U.S. PATENT DOCUMENTS

| | | | |
|---|---|---|---|
| 3,206,358 | 9/1965 | Stevenson | 167/53 |
| 3,234,002 | 2/1966 | Weed | 71/2.6 |
| 3,249,419 | 5/1966 | Martin | 71/2.5 |
| 3,544,677 | 12/1970 | Lapham et al. | 424/17 |
| 3,609,158 | 9/1971 | Torba | 260/295 R |
| 3,766,195 | 10/1973 | Bimber et al. | 260/295 R |
| 3,814,774 | 6/1974 | Whitaker et al. | 260/297 R |
| 3,883,541 | 5/1975 | Hamilton | 260/295 R |
| 3,923,822 | 12/1975 | Domenico | 260/297 R |
| 4,066,438 | 1/1978 | Johnston et al. | 71/94 |

FOREIGN PATENT DOCUMENTS 1274401  8/1968  Fed. Rep. of Germany ...... 260/297 R

OTHER PUBLICATIONS

Cava et al., J. Org. Chem. vol. 23 (1614–1616) (1958).

*Primary Examiner*—Richard Raymond
*Attorney, Agent, or Firm*—S. Preston Jones; Ronald G. Brookens; C. Kenneth Bjork

[57] ABSTRACT

Compounds are prepared which correspond to the formula

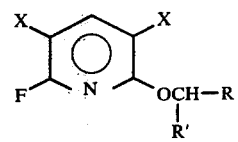

wherein X represents chloro, bromo or iodo; R' represents hydrogen or methyl and R represents carboxy (—COOH), the alkyl esters thereof (—COOR$^6$ wherein R$^6$ represents alkyl of 1 to 8 carbon atoms, (2-alkoxyethoxy)carbonyl (—COOCH$_2$CH$_2$OR$^2$) or (1-methyl-2-alkoxyethoxy)carbonyl

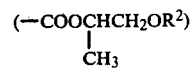

wherein R$^2$ represents alkyl of 1 to 4 carbon atoms) or the metal salts thereof (—COOMe wherein Me represents ammonium or substituted ammonium ion (N+H(R$^6$)$_3$ wherein each R$^6$ independently represents hydrogen, alkyl of 1 to 4 carbon atoms or hydroxyalkyl of 2 to 3 carbon atoms), alkali metal, alkaline earth metal, aluminum or a transition group metal); alkanoyloxymethyl (—CH$_2$OCOR$^2$); (2,2-dichloropropionyloxy)methyl (—CH$_2$OCOC(Cl)$_2$CH$_3$); alkoxymethyl (—CH$_2$OR$^2$); phenoxymethyl (—CH$_2$Oφ); (2-alkoxyethoxy)methyl (—CH$_2$OCH$_2$CH$_2$OR$^2$); hydroxyalkyl (—R$^3$OH wherein R$^3$ represents alkylene of from 1 to 6 carbon atoms); 3-hydroxy-1-propenyl (—CH=CHCH$_2$OH); 1,2-dihydroxyethyl

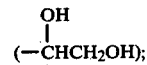

1-(2-hydroxyethoxy)methyl (—CH$_2$—O—CH$_2$CH$_2$OH); (2-(2-hydroxyethoxy)ethoxy)methyl (—CH$_2$OCH$_2$CH$_2$OCH$_2$CH$_2$OH); carbamoyl (—CONR$^4$R$^4$ wherein each R$^4$ independently represents hydrogen or alkyl of 1 to 8 carbon atoms); (carboxymethyl)carbamoyl (—CONHCH$_2$COOH); (2-hydroxyethyl)-carbamoyl (—CONR$^4$CH$_2$CH$_2$OH); or (carbamoyloxy)methyl (—CH$_2$OCONHR$^5$ wherein R$^5$ is alkyl of 1 to 4 carbon atoms or phenyl). These compounds have been found to be effective pre- and post-emergent herbicides and some as intermediates in preparing compounds which are effective pre- and post-emergent herbicides and as active agents in compositions used as herbicides.

43 Claims, No Drawings

6-FLUORO-3,5-DIHALO-2-PYRIDYLOXY COMPOUNDS

CROSS-REFERENCE TO RELATED APPLICATIONS

This is a continuation-in-part of application Ser. No. 765,190, filed Feb. 3, 1977, now abandoned, which is in turn a continuation of application Ser. No. 568,339, filed Apr. 15, 1975, now abandoned, which in turn is a continuation-in-part of application Ser. No. 460,010, filed Apr. 11, 1974, now abandoned.

PRIOR ART

Polyhalopyridyloxy compounds are well-known in the prior art. Various 6-fluoro pyridyloxy compounds are taught in British Pat. No. 1,161,492. Polyfluoro pyridyloxy compounds are taught in British Pat. No. 1,159,036. Various halogenated 2-pyridyloxy-acetic acids are taught by Cava et al., J. Org. Chem. 1958 1614–1616; Wain et al. "The Chemistry and Mode of Action of Plant Growth Substances" (1956) Butterworths Scientific Publications, London, pages 117–133; Cava, "Final Report by The Ohio State University Research Foundation" on Synthesis of Heterocyclic Compounds (1957) pages 1–27; and Gorter, Physiologia Plantarium, 10 1957, pages 858–868. U.S. Pat. Nos. 3,249,419; 3,251,849; 3,545,955 and 3,256,290 teach various halogenated pyridyloxy compounds. U.S. Pat. No. 3,249,619 is directed to various halopyridyloxy carbamates and U.S. Pat. No. 3,535,328. Other references of interest include U.S. Pat. No. 2,676,926 which broadly teaches halopyridyloxyalkyl; U.S. Pat. Nos. 3,249,619 and 3,409,624; Hertog et al., Rec. Trav. Chem 70 (1951) pages 182–190; Belgian Patent No. 630,125; and Chemical Abstracts 68 21842v.

SUMMARY OF THE INVENTION

The present invention is directed to novel compounds corresponding to the formula

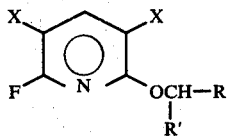

wherein X represents chloro, bromo or iodo; R' represents hydrogen or methyl and R represents carboxy (—COOH), the alkyl esters thereof (—COOR$^6$ wherein R$^6$ represents alkyl of 1 to 8 carbon atoms, (2-alkoxyethoxy)carbonyl (—COOCH$_2$CH$_2$OR$^2$) or (1-methyl-2-alkoxyethoxy)carbonyl

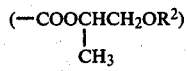

wherein R$^2$ represents loweralkyl of 1 to 4 carbon atoms) or the metal salts thereof (—COOMe wherein Me represents ammonium or substituted ammonium ion (N+H(R$^6$)$_3$ wherein each R$^6$ independently represents hydrogen, alkyl of 1 to 4 carbon atoms or hydroxyalkyl of 2 to 3 carbon atoms), alkali metal, alkaline earth metal, aluminum or a transition group metal); alkanoyloxymethyl (—CH$_2$OCOR$^2$); (2,2-dichloropropionyloxy)methyl (—CH$_2$OCOC(Cl)$_2$CH$_3$); alkoxymethyl (—CH$_2$OR$^2$); phenoxymethyl (—CH$_2$Oφ); (2-alkoxyethoxy)-methyl (—CH$_2$OCH$_2$CH$_2$OR$^2$); hydroxyalkyl (—R$^3$OH wherein R$^3$ represents alkylene of from 1 to 6 carbon atoms); 3-hydroxy-1-propenyl (—CH=CHCH$_2$OH); 1,2-dihydroxyethyl

1-(2-hydroxyethoxy)methyl (—CH$_2$—O—CH$_2$CH$_2$OH); (2-(2-hydroxyethoxy)ethoxy)methyl (—CH$_2$OCH$_2$CH$_2$OCH$_2$CH$_2$OH); carbamoyl (—CONHR$^4$R$^4$ wherein each R$^4$ independently represents hydrogen or alkyl of 1 to 8 carbon atoms); (carboxymethyl)carbamoyl (—CONHCH$_2$COOH); (2-hydroxyethyl)carbamoyl (—CONR$^4$CH$_2$—CH$_2$OH); or (carbamoyloxy)—methyl (—CH$_2$OCONHR$^5$ wherein R$^5$ is alkyl of 1 to 4 carbon atoms or phenyl).

The 6-fluoro-3,5-dihalo-2-pyridyloxy compounds of the present invention are crystalline solids or oils which are of low solubility in water and of moderate solubility in common organic solvents. These compounds have been found to be very effective pre- and post-emergent herbicides or as intermediates in the preparation of compounds which are effective pre- and post-emergent herbicides or as active agents in compositions employed as herbicides.

The term "alkyl" as employed in the present specification and claims designates either straight or branched chain alkyl radicals.

The 6-fluoro-3,5-dihalo-2-pyridyloxy compounds of the present invention can be prepared by a variety of methods as set forth hereinbelow.

Those compounds wherein R is alkyl carboxylic acid ester (—COOR$^6$ wherein R$^6$ is alkyl of 1 to 8 carbon atoms) can be prepared by the reaction of an appropriate α-bromo (or chloro) acetic or propionic acid ester with an appropriate 6-fluoro-3,5-dihalo-2-pyridinol in the presence of sodium or potassium metal, a loweralkanol and a co-solvent such as, for example, dimethyl formamide or dimethyl sulfoxide.

In carrying out this reaction, one mole of the sodium or potassium metal is first dissolved in a loweralkanol and one mole of the pyridinol added thereto, followed by the addition of an excess of the ester reactant in one of the co-solvents listed hereinabove. The mixture is refluxed for about 1 to about 8 hours and at the completion of the reaction, the solvent is removed and the residue quenched with water. The product precipitates out and can be recovered by filtration or other conventional separatory procedures, and if desired, it can be purified by recrystallization from a solvent such as benzene or hexane.

Those compounds wherein R is carboxy (—COOH) can be prepared by the hydrolysis of the corresponding alkyl ester.

In carrying out this reaction, the ester reactant in a reaction medium or solvent is treated, under reflux conditions, with an alkali metal hydroxide for a period of time of from about 1 to about 4 hours. Thereafter, the reaction product is acidified with a mineral acid such as hydrochloric or sulfuric acid and the desired product recovered by filtration or other conventional separatory procedure.

The reaction consumes the reactants in stoichiometric proportions, i.e., one equivalent of the ester reactant per equivalent of the alkali metal hydroxide and mineral acid. However, due to the nature of the hydrolysis reaction, it is preferred that a slight excess of the alkali metal hydroxide and mineral acid be employed. If desired, the product can be purified by recrystallization from a solvent such as, for example, nitromethane, carbon tetrachloride, n-hexane, cyclohexane, chloroform, benzene, methanol, ethanol or a methanol-water mixture or by the use of a combination of any of these solvents and/or by the sequential use of one or more of these solvents.

Representative reaction mediums, i.e., solvents for carrying out the reaction include, for example, water, dioxane, dimethylformamide, dimethylsulfoxide, tetrahydrofuran, and other conventional ether solvents. Representative alkali metal hydroxides for use as reactants are the hydroxides of sodium, potassium, cesium, lithium and rubidium.

The compounds of the present invention wherein R is a carboxylic acid salt (—COOMe) are prepared by the reaction of the appropriate 6-fluoro-3,5-dihalopyridyloxy carboxylic acid with an appropriate metal hydroxide or carbonate. The term "salt" as employed in the present specification and claims designates the reaction products of basic compounds with the acid functional group —COOH. Such salts can be represented by the formula —COOMe wherein Me represents ammonium and substituted ammonium such as, for example, methyl ammonium, ethyl ammonium, n-propyl ammonium, n-butyl ammonium, dimethyl ammonium, diethyl ammonium, di-n-propyl ammonium, diisopropyl ammonium, di-n-butyl ammonium, ethanol ammonium, diisopropanol ammonium, methylethyl ammonium, methyldiethyl ammonium, ethylbutyl ammonium, methylethanol ammonium, methyldiisopropanol ammonium and the like; the alkali metals such as sodium, lithium, potassium, cesium or rubidium; the alkaline earth metals such as calcium, barium or strontium; and the heavy metals including antimony, zinc, bismuth, cadmium, cerium, chromium, cobalt, copper and other metals having a density of above 4.

In carrying out the reaction, substantially equivalent proportions of the acid and base are mixed together in a suitable solvent such as an alcohol-water mixture whereupon a reaction takes place with the formation of the desired salt product and water-by-product. The salt may or may not be soluble in the reaction medium. If insoluble, it may be recovered by filtration; if soluble, it may be recovered by vaporizing off the solvent and water. The salt may be purified, if desired, by conventional methods.

Salts of metals which form difficultly soluble hydroxides, such as, for example, copper, may be prepared by an alternative procedure wherein an alkali metal salt of the desired compound is reacted with a soluble mineral acid salt of said metal, such as the chloride or nitrate to produce the said metal salts of acid compound. In such preparation, substantially equivalent proportions of the alkali metal salt compound and said metal salt of a mineral acid are stirred together in water or a water-alcohol solvent at room temperature or with gentle warming for from 0.5 hour to several hours whereupon the desired metal salt compound usually precipitates in the reaction mixture. The latter may be recovered by filtration and purified, if desired, by conventional procedures.

Those compounds wherein R is alkoxy alkyl carboxylic esters (—COOR$^6$) wherein R$^6$ is (2-alkoxyethoxy)—carbonyl (—COOCH$_2$CH$_2$OR$^2$) or (1-methyl-2-alkoxyethoxy)—carbonyl

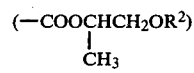

can be prepared by the reaction of an appropriate 6-fluoro-3,5-dihalo-2-pyridyloxy carboxylic acid with an appropriate alkyl ether of ethylene glycol or propylene glycol in the presence of a solvent such as, for example, toluene and a catalyst, such as, for example, p-toluene sulfonic acid.

The reaction scheme can be exemplified as follows:

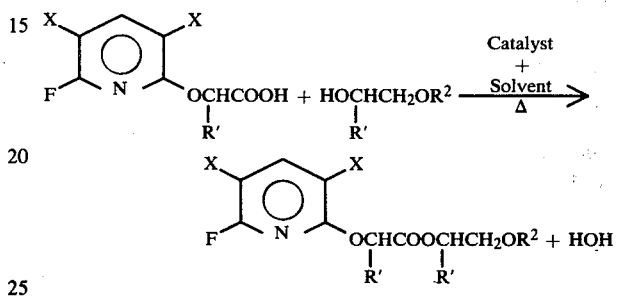

In carrying out this reaction, substantially equimolar amounts of the acid and glycol reactants are mixed in the solvent with about 2 to 3 weight percent of the catalyst and the mixture heated under reflux conditions for a period of from about 2 to about 10 hours or more. The water is azeotroped out as formed under these conditions and the speed of its removal controls the overall reaction time. Thereafter, the reaction product is washed with a dilute alkaline solution such as, for example, sodium bicarbonate, potassium bicarbonate or the like, followed by a water wash. The mixture is dried over magnesium sulfate and filtered under vacuum. The solvent is thereafter removed by evaporation under reduced pressure or other such conventional separatory procedures.

The compounds wherein R is alkoxymethyl (—CH$_2$OR$^2$); phenoxymethyl (—CH$_2$O$\phi$); (2-alkoxyethoxy)-methyl (—CH$_2$OCH$_2$CH$_2$OR$^2$) or (2-(2-hydroxyethoxy)ethoxy)methyl (—CH$_2$OCH$_2$CH$_2$OCH$_2$CH$_2$OH) can be prepared by reacting an appropriate 2,6-difluoro-3,5-dihalopyridine with an appropriate glycol ether in the presence of sodium hydride.

The reaction is initiated by slowly bringing together a mixture of the pyridine and glycol ether reactants and solvent washed alkali hydride (as a solvent slurry). The reaction mixture, at room temperature, is stirred until the foaming which occurs ceases and then stirred for an additional ~10 minutes and diluted with water. This mixture is extracted with a solvent such as, for example, methylene chloride, and diluted with water. This mixture is extracted with a solvent such as, for example, methylene chloride, ether, hexane, benzene or chloroform. The extract is dried, filtered and concentrated under a reduced pressure. The reaction consumes the reactants in substantially stoichiometric proportions, i.e. one equivalent of the pyridine reactant per equivalent of the glycol ether and alkali hydride. However, since the glycol ether can act as a reaction medium, it is preferred to use a sufficient excess of this reactant so that it can function as the reaction medium.

The compounds wherein R is alkanoyloxymethyl (—CH$_2$OCOR$^2$) or (2,2-dichloropropionyloxy)methyl (—CH₂OCOC(Cl)₂CH₃) can be prepared by reacting an appropriate 2-(3,5-dihalo-6-fluoro-2-pyridyloxy) ethanol and an appropriate acid chloride

in the presence of a base such as pyridine or a tertiary amine to act as a reaction medium and an acid acceptor.

The reaction is initiated by slowly bringing together a mixture of the base and pyridyloxyethanol reactant and the acid chloride, at room temperature. The mixture is stirred for from about 1 to about 16 hours and filtered to remove any insoluble materials. The mixture is concentrated under a reduced pressure and the residual material crystallized with a loweralkanol-water mixture. The reaction consumes the reactants in substantially stoichiometric proportions, i.e. one equivalent of the pyridyloxy ethanol reactant per equivalent of the acid chloride and the use of such proportions is preferred.

The compounds wherein R is hydroxyalkyl (—R³OH), 3-hydroxy-1-propenyl (—CH=CHCH₂OH), 1,2-dihydroxyethyl (—CH—OH—CH₂OH) or (2-hydroxyethoxy)methyl (—CH₂—O—CH₂—CH₂OH) can be prepared by reacting an appropriate 2,6-difluoro-3,5-dihalopyridine with an appropriate diol (HO-M-OH wherein M is loweralkylene, vinylene, 1-propenylene, 2-hydroxy propylene or oxydiethylene in the presence of an alkali metal hydroxide and a diol as a solvent.

The reaction is initiated by slowly bringing the reactants together in the presence of a base and a diol as a solvent for a period of time of from about 5 minutes to about 1 hour. The reaction consumes the reactants in substantially stoichiometric proportions, i.e., one equivalent of the pyridine reactant per equivalent of the diol and alkali metal hydroxide. However, since the diol compound can act as a reaction medium (solvent), it is preferred to use a sufficient excess of this reactant so that it can function as the reaction medium. The reaction is carried out at a temperature of about 65°–90° C. At the completion of the reaction, the reaction mixture is cooled and diluted with water. The insoluble by-products are removed using conventional separatory techniques and the remaining mixture extracted with a solvent such as, for example, methylene chloride, ether, hexane, benzene or chloroform. The extract is dried, if desired, and the solvent removed by conventional techniques such as, for example, evaporation under a reduced pressure. The product can be purified by recrystallization from a solvent such as one of those listed hereinbefore.

The compounds wherein R is carbamoyl (—CONR⁴R⁴) can be prepared by the direct amination of the corresponding carboxylic acid alkyl ester compound with ammonia or an amine.

In carrying out the reaction, the ester and ammonia or amine reactants in a solvent or reaction medium are contacted together in any suitable fashion and maintained together, under agitation, for a period of time of from about 1 to about 20 hours. When one of the reactants is a highly volatile material, it is preferred that a closed reaction vessel be employed to prevent loss of this reactant. The reaction can be carried out at a temperature of from about room temperature to about 100° C. Upon completion of the reaction, the excess ammonia or amine reactant is removed by flashing or evaporation under reduced pressure. The solid material is thereafter recrystallized from solvents listed hereinbefore.

The compounds wherein R is (carboxymethyl) carbamoyl (—CONHCH₂COOH) can be prepared by the reaction of the acid chloride of the appropriate 6-fluoro-3,5-dihalo-pyridyloxy acetic acid with sodium or potassium salt of glycine in an aqueous solution.

In carrying out this reaction, one mole of glycine and 3 moles of an alkali metal hydroxide such as sodium or potassium hydroxide are dissolved in about 36 moles of water. A solution of one mole of the acid chloride of the appropriate pyridyloxy acetic acid in 750–800 milliliters of benzene is thereafter added with vigorous stirring over a 10 to 15 minute period. During the addition the temperature is held at about 2°–5° C. and thereafter the reaction mixture is allowed to come to room temperature and stirred at this temperature for about 2–3 hours. At the end of this time, the aqueous layer is separated and acidified. The product is a solid and precipitates out and is recovered by filtration and washed and dried.

The compounds wherein R is (2-hydroxyethyl)-carbamoyl(—CONR⁴CH₂CH₂OH) can be prepared by the reaction of the acid chloride of the appropriate 6-fluoro-3,5-dihalopyridyloxy acetic acid with an appropriate amino ethanol in an organic solvent such as benzene or hexane.

In carrying out the reaction, a solution of about one mole of the acid chloride reactant in about 1.5 liters of a benzene-hexane mixture (50 percent each) is added at a temperature of about 25° C. over a 20–30 minute period to a solution of 2 moles of the aminoethanol in 1.0 liter of the same solvent mixture. The reaction mixture is held with stirring at 25° C. for about 1.0 hour. At the completion of the reaction, the insoluble amine hydrochloride by-product is removed by decantation or other conventional separatory procedures and the solvent phase cooled to precipitate the desired product. The product is washed and dried and if desired can be further purified by recrystallization from hexane.

The compounds wherein R is (carbamoyloxy)-methyl (—CH₂OCONHR⁵) can be prepared by reacting an appropriate 2-(3,5-dihalo-6-fluoro-2-pyridyloxy) ethanol and an appropriate loweralkyl or phenyl isocyanate in the presence of a reaction medium such as dichloromethane and a catalytic amount of an amine such as triethylamine to act as a reaction medium and an acid acceptor.

The reaction is initiated by slowly bringing together a mixture of the base and pyridyloxyethanol reactant and the isocyanate, at room temperature. The mixture is stirred for from about 1 to about 16 hours, filtered and concentrated. The mixture is thereafter extracted with a solvent such as a loweralkanol-water mixture and dichloromethane or dried. The reaction consumes the reactants in substantially stoichiometric proportions, i.e. one equivalent of the pyridyloxyethanol reactant per equivalent of the isocyanate and the use of such proportions is preferred.

DESCRIPTION OF SOME PREFERRED EMBODIMENTS

In order that the present invention may be more fully understood, the following examples are given primarily by way of illustration and should not be construed as limitations upon the overall scope of the present invention.

EXAMPLE I

Ethyl(3,5-dichloro-6-fluoro-2-pyridyloxy)-acetate

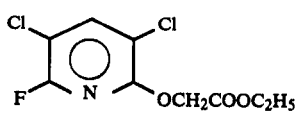

A solution was prepared by dissolving 6.9 grams (0.3 mole) of sodium metal in 700 milliliters of 95 percent ethanol. To this solution was added with stirring 54.5 grams (0.3 mole) of 3,5-dichloro-6-fluoro-2-pyridinol. Thereafter 58.5 grams (0.35 mole) of ethyl bromoacetate was added and the mixture refluxed for 5 hours. At the completion of the reaction, the ethanol was distilled off and the residue poured into water. The solid which precipitated was filtered off and taken up in hexane and dried with activated carbon and anhydrous sodium sulfate. The mixture was filtered and the hexane removed and the ethyl-(3,5-dichloro-6-fluoro-2-pyridyloxy) acetate product was recovered by distillation. The product was a white waxy solid which boiled at 135°–170° C. (M.P. 63.5°–64° C.)

EXAMPLE II (3,5-Dichloro-6-fluoro-2-pyridyloxy) acetic acid

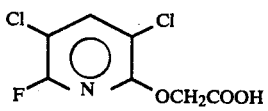

A mixture of 17 grams (0.06 mole) of ethyl-(3,5-dichloro-6-fluoro-2-pyridyloxy)acetate in 90 milliliters of commercial grade ethanol and 2.8 grams of sodium hydroxide in 25 milliliters of water was refluxed for ~20 minutes. Thereafter 5.9 cubic centimeters of concentrated hydrochloric acid was added thereto and the mixture stirred and cooled for 15 minutes. The mixture was filtered to recover the solid which precipitated and the solid was extracted exhaustively with boiling hexane followed by extraction with a hexane-benzene mixture. After drying, the (3,5-dichloro-6fluoro-2-pyridyloxy) acetic acid product was recrystallized from hexane and was recovered in a yield of ~6 grams and melted at 140°–144° C. Upon analysis, the product was found to have carbon, hydrogen, chlorine and nitrogen contents of 36.04, 2.11, 29.28 and 5.64 percent, respectively, as compared with the theoretical contents of 35.03, 1.67, 29.54 and 5.83 percent, respectively, calculated for the above-named compound.

EXAMPLE III 2-(3,5-Dichloro-6-fluoro-2-pyridyloxy)ethanol

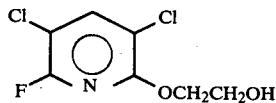

To a solution of 12 grams (0.065 mole) of 3,5-dichloro-2,6-difluoropyridine in 35 milliliters of ethylene glycol was added over a 10 minute period 2.7 grams of anhydrous sodium hydroxide in 40 milliliters of ethylene glycol. The reaction mixture was maintained at ~70° C. with agitation for 10 minutes, cooled and poured into water. The insoluble material is removed by filtration and the filtrate extracted with methylene chloride and dried. The solid 2-(3,5-dichloro-6-fluoro-2-pyridyloxy) ethanol product was crystallized from hexane and recovered in a yield of 9 grams (61 percent of theoretical). The product melted at 65°–67° C. and was found by analysis to have carbon, hydrogen, chlorine and nitrogen contents of 37.4, 3.1, 31.5 and 6.4 percent, respectively, as compared with the theoretical contents of 37.2, 2.7, 31.4 and 6.2 percent, respectively, calculated for the above-named compound.

EXAMPLE IV

Mixture of 2-(3,5-dichloro-6-fluoro-2-pyridyloxy)-1-propanol and 1-(3,5-dichloro-6-fluoro-2-pyridyloxy)-2-propanol

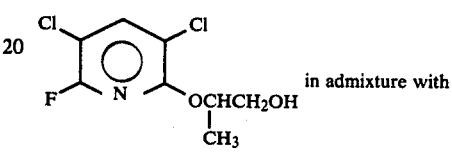 in admixture with

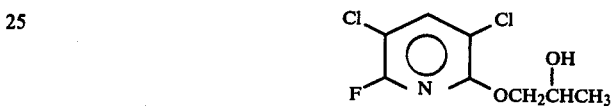

To a solution of 14 grams (0.076 mole) of 3,5-dichloro-2,6-difluoropyridine in 40 milliliters of propylene glycol was added in ~5 minutes 3.12 grams (0.078 mole) of sodium hydroxide in 50 milliliters of propylene glycol. The reaction mixture was maintained at ~70° C. with agitation for ~10 minutes. The mixture was cooled and poured into 300 milliliters of water and thereafter extracted thoroughly with methylene chloride. The extract was dried and the methylene chloride removed by evaporation. The residue was taken up in boiling hexane, passes over activated charcoal, dried and cooled. The solid product, a mixture of 2-(3,5-dichloro-6-fluoro-2-pyridyloxy)-1-propanol and 1-(3,5-dichloro-6-fluoro-2-pyridyloxy)-2-propanol, which precipitated, was recovered by filtration in a yield of 10.5 grams (56.1 percent of theoretical). The product melted at 47°–50° C. and was found by analysis to have carbon, hydrogen, chlorine and nitrogen contents of 40.5, 3.6, 29.1 and 6.5 percent, respectively, as compared with the theoretical contents of 40.0, 3.4, 29.5 and 5.8 percent, respectively, calculated for the above-named compounds.

EXAMPLE V 3-(3,5-Dichloro-6-fluoro-2-pyridyloxy)-1,2-propanediol

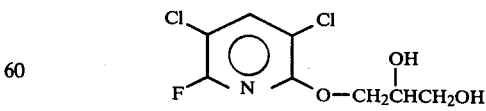

To a solution of 12.9 grams (0.07 mole) of 3,5-dichloro-2,6-difluoropyridine in 50 milliliters of glycerol was added over an 8 minute period 2.9 grams of sodium hydroxide in 25 milliliters of glycerol. The mixture was maintained at ~85° C. for ~17 minutes, cooled and poured into 200 milliliters of cold water.

The solid which precipitated was air dried and taken up in benzene, dried and most of the benzene was removed by evaporation under reduced pressure. The residue was mixed with hexane and cooled and the crystalline 3-(3,5-dichloro-6-fluoro-2-pyridyloxy)-1,2-propanediol product which precipitated was recovered by filtration. The product was covered in a yield of 10 grams (56 percent of theoretical). The product melted at 78°–80° C. and was found upon analysis to have carbon, hydrogen, chlorine and nitrogen contents of 37.5, 2.9, 27.6 and 5.6 percent, respectively, as compared with the theoretical contents of 37.5, 3.2, 27.7 and 5.5 percent, calculated for the above-named compound.

EXAMPLE VI 4-(3,5-Dichloro-6-fluoro-2-pyridyloxy)-2-buten-1-ol

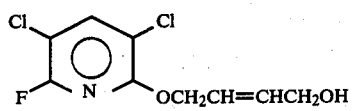

To a solution of 11 grams (0.06 mole) of 3,5-dichloro-2,6-difluoropyridine in 35 milliliters of ethylene glycol was added over a 15 minute period 2.44 grams of sodium hydroxide in 35 milliliters of butenediol(2-butene-1,4-diol). The mixture was heated to ~70° C. and agitated for ~3½ hours. Thereafter the mixture was poured into water and extracted with hot hexane. Most of the hexane was removed and upon cooling the 4-(3,5-dichloro-6-fluoro-2-pyridyloxy)-2-buten-1-ol product precipitated out. The product was recovered in a yield of 9 grams (60 percent of theoretical) and melted at 30° C. Upon analysis, the product was found to have carbon, hydrogen, chlorine and nitrogen contents of 43.3, 2.8, 27.8 and 5.6 percent, respectively, as compared with the theoretical contents of 42.9, 3.2, 28.1 and 5.6 percent, respectively, as calculated for the above named structure.

EXAMPLE VII

Ethyl[2-(3,5-Dichloro-6-fluoro-2-pyridyloxy)]-propionate

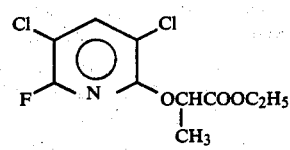

A solution was prepared by dissolving 1.84 grams (0.08 mole) of sodium metal in 140 milliliters of 28 percent ethanol. To this solution was added 14.6 grams (0.08 mole) of 3,5-dichloro-6-fluoro-2-pyridinol. The solution was warmed and 60 milliliters of N,N-dimethylformamide was added thereto. The solution was further heated to remove about ¾ of the ethanol. To the remaining solution was added 15.5 grams (0.85 mole) of ethyl bromopropionate followed by an additional 40 milliliters of N,N-dimethylformamide. The mixture was refluxed at 118° C. for 20 minutes, cooled and poured into water. The mixture was extracted with hexane and the hexane thereafter removed by evaporation. The residue was distilled under reduced pressure and the ethyl[2-(3,5-dichloro-6-fluoro-2-pyridyloxy)]propionate was recovered as an oil in a yield of 17.7 grams (78.3 percent of theoretical) and had a boiling point at 2.4 millimeters of mercury at 127° C. Upon analysis, the product was found to have carbon, hydrogen, chlorine and nitrogen contents of 42.0, 3.1, 25.1 and 5.2 percent, respectively, as compared with the theoretical contents of 42.6, 3.6, 25.1 and 4.9 percent, respectively, calculated for the above named compound.

EXAMPLE VIII 4-(3,5-Dichloro-6-fluoro-2-pyridyloxy)-1-butanol

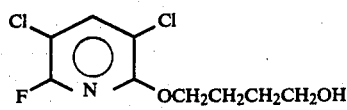

To a solution of 11 grams (0.06 mole) of 3,5-dichloro-2,6-difluoropyridine in 35 milliliters of 1,4-butanediol was added over a 10 minute period 2.44 grams of sodium hydroxide in 35 milliliters of ethylene glycol. The temperature was maintained at between 50°–60° C. during the addition. The mixture was stirred for 1¾ hours while the temperature was maintained between 60°–65° C. The reaction mixture was cooled and poured into water and thereafter extracted three times with 135 milliliter portions of hot hexane. The mixture was heated to remove most of the hexane by evaporation, cooled and filtered to remove the solid 4-(3,5-dichloro-6-fluoro-2-pyridyloxy)-1-butanol product. The product was recovered in a yield of 11 grams (73 percent of theoretical) and melted at 38°–39° C. Upon analysis, the product was found to have carbon, hydrogen, chlorine and nitrogen contents of 43.2, 3.7, 27.9 and 5.7 percent, respectively, as compared with the theoretical contents of 42.5, 3.9, 27.9 and 5.5 percent, respectively, as calculated for the above named compound.

EXAMPLE IX (3,5-Dichloro-6-fluoro-2-pyridyloxy)-acetyl chloride

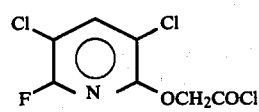

A solution was prepared by admixing 8.6 grams (0.036 mole) of 3,5-dichloro-6-fluoro-2-pyridyloxy acetic acid in 15 milliliters of thionyl chloride. The mixture was refluxed for about 50 minutes. At the completion of the reaction, the excess thionyl chloride was removed by distillation. The liquid residue was cooled and the crystals which formed were separated. The (3,5-dichloro-6-fluoro-2-pyridyloxy)acetyl chloride product was recovered in a yield of 8.4 grams (92 percent of theoretical). Upon analysis, the product was found to have carbon, hydrogen, chlorine and nitrogen contents of 32.9, 0.9, 41.9 and 5.3 percent, respectively as compared with the theoretical contents of 32.8, 0.4, 41.4 and 5.5 percent, respectively, as calculated for the above-named compound.

EXAMPLE X

N-[(3,5-Dichloro-6-fluoro-2-pyridyloxy)-acetyl]glycine

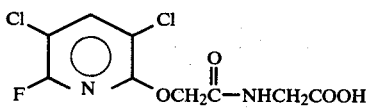

A solution was prepared by admixing 2.93 grams (0.039 mole) of glycine with 4.67 grams (0.117 mole) of sodium hydroxide in 117 milliliters of water. To this solution was added 10.0 grams of (3,5-dichloro-6-fluoro-2-pyridyloxy)acetyl chloride in 30 milliliters of benzene. The mixture was allowed to stand at a temperature of ~2°-5° C. for about 10 minutes and the mixture was warmed to room temperature and stirred for about 30 minutes. The reaction mixture was diluted with additional benzene and the aqueous layer which formed was removed and acidified. The solid which precipated was removed by filtration, dried and recrystallized from 50 percent ethanol. The N-[(3,5-dichloro-6-fluoro-2-pyridyloxy)acetyl]glycine product was recovered in a yield of 5.0 grams and melted at 155°-157° C. and upon analysis was found to have carbon, hydrogen, chlorine and nitrogen contents of 35.7, 2.1, 24.2 and 8.7 percent, respectively as compared with the theoretical contents of 36.5, 2.4, 23.9 and 9.4 percent, respectively, calculated for the above named compound.

EXAMPLE XI 2-(3,5-Dichloro-6-fluoro-2-pyridyloxy)-ethyl 2,2-dichloropropionate

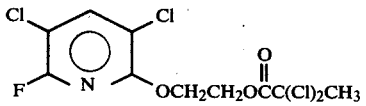

A solution was prepared by admixing 250 milliliters of acetonitrile, 55.3 grams (0.4 mole) of potassium carbonate, 42.5 grams (0.16 mole) of 2-(3,5-dichloro-6-fluoro-2-pyridyloxy)ethanol and 32.3 grams (0.2 mole) of 2,2-dichloropropionyl chloride. This mixture was stirred at room temperature for 4 days. The solids which formed were removed by filtration and the filtrate was concentrated under a reduced pressure. The residual material which remained was dissolved in hexane and washed with water. The hexane was removed under a reduced pressure to yield a pale-orange liquid having a refractive index of n/25D=1.5239. The product was confirmed to be 2-(3,5-dichloro-6-fluoro-2-pyridyloxy)ethyl 2,2-dichloro propionate by its infrared and nuclear magnetic resonance spectrums.

EXAMPLE XII 2-(3,5-Dichloro-6-fluoro-2-pyridyloxy)ethyl acetate

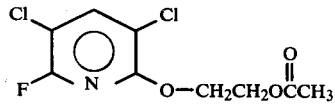

A solution was prepared by admixing 80 milliliters of pyridine and 11.25 grams (0.05 mole) of 2-(3,5-dichloro-6-fluoro-2-pyridyloxy)ethanol to this solution was added dropwise 3.93 grams (0.05 mole) of acetyl chloride. The reaction mixture was stirred at room temperature overnight and thereafter poured into a mixture of crushed ice and concentrated hydrochloric acid. The resulting mixture was extracted twice with 100 milliliter portions of dichloromethane. The extracts were combined and dried over anhydrous sodium sulfate, filtered and concentrated under reduced pressure. The oil which remained as a residue was vacuum distilled yielding 6.45 grams (48 percent of theoretical) of 2-(3,5-dichloro-6-fluoro-2-pyridyloxy) ethyl acetate as a light amber oil. The product had a boiling point of 93°-106° C. at 0.4 millimeters of mercury (mm). Upon analysis, the product was found to have carbon, hydrogen and nitrogen contents of 40.47, 3.14 and 5.42 percent, respectively, as compared with the theoretical contents of 40.32, 3.01 and 5.22 percent, respectively, calculated for the above named structure.

EXAMPLE XIII

2-[2-(2-Butoxyethoxy)ethoxy]-3,5-dichloro-6-fluoropyridine

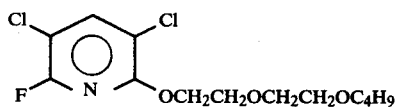

A mixture was prepared by admixing 12.9 grams (0.07 mole) of 3,5-dichloro-2,6-difluoropyridine, 100 milliliters of diethyleneglycol n-butyl ether and 3.3 grams (0.75 mole) of a hexane slurry of sodium hydride. The sodium hydride was a 53 percent oil dispersion and had been washed 3 times with 10 milliliter portions of hexane. Considerable foaming occurred and after foaming ceased, the reaction mixture was stirred for ~10 minutes at room temperature and thereafter diluted with 200 milliliters of water. The mixture was extracted 3 times with 100 milliliter portions of hexane, the extracts combined and dried over anhydrous sodium sulfate, filtered and concentrated under reduced pressure. The oil which remained as a residue was vacuum distilled to yield 14.3 grams of 2-[2-(2-butoxyethoxy)ethoxy]-3,5-dichloro-6-fluoropyridine as a water-white product. The product had a boiling point of 113°-124° C. at 0.3 millimeters of mercury (mm). Upon analysis, the product was found to have carbon, hydrogen and nitrogen contents of 47.55, 5.37 and 4.36 percent, respectively, as compared with the theoretical contents of 47.87, 5.56 and 4.29 percent, respectively, as calculated for the above named compound.

EXAMPLE XIV 2-(3,5-Dichloro-6-fluoro-2-pyridyloxy)-ethyl-N-phenyl carbamate

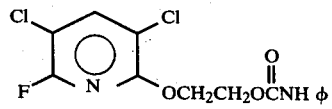

A mixture was prepared by admixing 80 milliliters of dichloromethane, 5.95 grams (0.05 mole) of phenyl isocyanate and 11.25 grams (0.05 mole) of 2-(3,5-dichloro-6-fluoro-2-pyridyloxy)ethanol and 5 drops of triethylamine. The mixture was allowed to sit overnight at room temperature. The solid precipitate which occurred was removed by filtration and the filtrate was concentrated under a reduced pressure. The oil which remained as a residue was crystallized from an ethanol-water mixture. Two additional recrystallizations were carried out and the crystals were dried yielding 7.84 grams of 2-(3,5-dichloro-6-fluoro-2-pyridyloxy)ethyl-N-phenyl carbamate as the product. The product melted at 70°-75.5° C. An additional recrystallization was given as above and after drying the product melted at 75°-76.5° C. Upon analysis, the product was found to have carbon, hydrogen and nitrogen contents of 48.64, 3.27 and 7.98 percent, respectively, as compared with the theoretical contents of 48.71, 3.21 and 8.12 percent, respectively, calculated for the above named compound.

The following compounds of the present invention are prepared in accordance with the methods hereinbefore set forth:

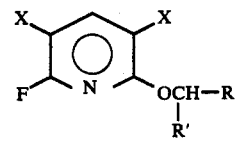

| X (both) | R' | R | M.W. | M.P. °C./B.P. °C. or Refractive indices |
|---|---|---|---|---|
| Cl | H | —COOCH$_3$ | 254.07 | 64°-65° |
| Br | H | —COOH | 328.94 | 165°-166° |
| I | H | —COOH | 422.93 | |
| Br | H | —COOCH$_3$ | 342.94 | |
| Br | H | —COOC$_2$H$_5$ | 356.96 | 69°-70° |
| Br | CH$_3$ | —COOH | 342.97 | |
| Br | H | —CN | 309.94 | |
| I | CH$_3$ | —COOC$_4$H$_9$ | 488.02 | |
| Cl | CH$_3$ | —COOH | 254.08 | 152°-153° |
| Br | CH$_3$ | —CONH$_2$ | 341.98 | |
| Cl | H | —CONH$_2$ | 239.05 | 134°-136° |
| Cl | H | —COONa | 262.03 | |
| Cl | H | —COO)$_3$Al | ~744.09 | |
| Cl | H | —COO)$_2$Cu | ~541.61 | |
| Cl | H | —COOK | 278.14 | |
| Br | CH$_3$ | —COO)$_2$Ca | ~724.00 | |
| Br | CH$_3$ | —COO)$_2$Co | ~742.86 | |
| I | H | —COO)$_2$Zn | ~909.22 | |
| I | CH$_3$ | —COO)$_3$Sb | ~1277.78 | |
| I | CH$_3$ | —CN | 417.95 | |
| Cl | H | —CN | 221.04 | 29°-33° |
| Cl | CH$_3$ | —COOC$_4$H$_9$ | 310.17 | |
| Cl | H | —COO(CH$_2$)$_2$OCH$_3$ | 298.10 | |
| Cl | H | —COO(CH$_2$)$_2$OC$_4$H$_9$ | 340.18 | |
| Cl | CH$_3$ | —COOCHCH$_2$OCH$_3$<br>               \|<br>               CH$_3$ | 326.15 | |
| Cl | CH$_3$ | —COOCHCH$_2$OC$_4$H$_9$<br>               \|<br>               CH$_3$ | 368.24 | |
| I | H | —COCl | 441.38 | |
| Cl | H | —(CH$_2$)$_4$CH$_2$OH | 282.16 | |
| Cl | H | —CH=CHOH | 238.07 | |
| Cl | CH$_3$ | —COCl | 271.47 | |
| Cl | H | —CH=CHCH$_2$OH | 252.09 | ~30° |
| Br | CH$_3$ | —CH=CHCH$_2$OH | 355.02 | |
| Cl | H | —CH$_2$OCH$_2$CH$_2$OH | 260.11 | oil |
| Cl | H | $\overset{\overset{O}{\|\|}}{-C}$NHCH$_3$ | 263.08 | 139.5°-140.5° |
| I | H | $\overset{\overset{O}{\|\|}}{-C}$NH(CH$_2$)$_3$CH$_3$ | 295.16 | 77°-78° |
| Cl | CH$_3$ | $\overset{\overset{O}{\|\|}}{-C}$NH(CH$_2$)$_3$CH$_3$ | 309.18 | |
| Cl | H | $\overset{\overset{O}{\|\|}}{-C}$NH(CH$_2$)$_7$CH$_3$ | 351.27 | 75°-77° |
| Cl | H | $\overset{\overset{O}{\|\|}}{-C}$N(CH$_3$)$_2$ | 255.09 | |
| Br | H | $\overset{\overset{O}{\|\|}}{-C}$NHCH$_2$COOH | 385.95 | |
| Cl | H | $\overset{\overset{O}{\|\|}}{-C}$—NCH$_2$CH$_2$OH<br>     \|<br>     CH$_3$ | 297.13 | 125° |

-continued

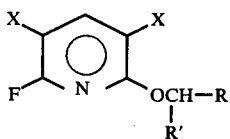

| X (both) | R' | R | M.W. | M.P. °C./B.P. °C. or Refractive indices |
|---|---|---|---|---|
| Br | CH$_3$ | —CNHCH$_2$CH$_2$OH (C=O) | 386.03 | |
| Cl | H | —CNHCH$_2$CH$_2$OH (C=O) | 283.10 | 114°–116° |
| Cl | H | —CH$_2$OCC$_2$H$_5$ (C=O) | 282.02 | 97°–107° at 0.5 mm |
| Cl | H | —CH$_2$OCCH(CH$_3$)$_2$ (C=O) | 296.03 | 91°–97° at 0.3 mm |
| Cl | H | —CH$_2$OCC(CH$_3$)$_3$ (C=O) | 310.04 | 90°–109° at 0.3 mm |
| Cl | H | —CH$_2$OCH$_3$ | 240.00 | 85°–95° at 0.5 mm |
| Cl | CH$_3$ | —CH$_2$OCH$_3$ | 254.01 | n/25D=1.5055 |
| Cl | H | —CH$_2$OC$_4$H$_9$-n | 282.03 | n/25D=1.4994 |
| Cl | H | —CH$_2$Oφ | 302.05 | n/25D=1.5631 |
| Cl | H | —CH$_2$OC$_2$H$_5$ | 235.01 | 80°–95° at 0.6 mm |
| Cl | H | —CH$_2$OCH$_2$CH$_2$OCH$_3$ | 284.02 | 120°–130° at 0.5 mm |
| Cl | H | —CH$_2$OCH$_2$CH$_2$OC$_2$H$_5$ | 298.03 | 108°–120° at 0.7 mm |
| Cl | H | —CH$_2$OCH$_2$CH$_2$OCH$_2$CH$_2$OH | 314.03 | 135°–150° at 0.5 mm |
| Cl | H | —CH$_2$OCNHCH$_3$ (C=O) | 283.01 | 80.5°–87° |
| Cl | CH$_3$ | —CH$_2$OCNHC$_4$H$_9$ (C=O) | 325.05 | |
| Cl | CH$_3$ | —CH$_2$OCNHC$_4$H$_9$ (C=O) | 507.95 | |

The following compounds are all quaternary ammonium compounds wherein R represents —COO$^{(-)}$N$^{(+)}$H(R$^6$)$_3$. For brevity, the positive and negative charges are not being placed on the ammonium salts. It is to be understood that such charges are encompassed herein.

| X (both) | R' | R | M.W. | M.P.°C./ B.B. °C. or Refractive indices |
|---|---|---|---|---|
| Br | H | —COONH$_4$ | 345.97 | |
| Cl | H | —COONH$_3$CH$_3$ | 271.08 | |
| Cl | H | —COONH$_3$C$_4$H$_9$ | 312.31 | |
| Br | H | —COONH$_2$(CH$_3$)$_2$ | 522.75 | |
| Cl | CH$_3$ | —COONH$_2$(C$_4$H$_9$)$_2$ | 383.29 | |
| Cl | H | —COONH$_2$(i-C$_3$H$_6$OH)$_2$ | 373.21 | |
| I | H | —COONH(C$_4$H$_9$)$_3$ | 624.28 | |
| Cl | H | —COONH$_2$C$_2$H$_4$OH | 301.10 | |
| Cl | H | —COONH$_2$(CH$_3$)C$_2$H$_5$ | 299.13 | |
| Cl | H | —COONH(CH$_3$)(C$_4$H$_9$)$_2$ | 383.29 | |
| Cl | CH$_3$ | —COONH(CH$_3$)(C$_3$H$_6$OH)$_2$ | 401.27 | |

In accordance with the present invention, it has been discovered that the 6-fluoro-3,5-dihalopyridyloxy compounds of the present invention are useful as pre- and post-emergent herbicides. In accordance with this invention, a method for controlling or inhibiting the growth of undesirable plant species is provided which comprises applying to plants, plant parts or their habitat, an effective or growth inhibiting amount of at least one of the 6-fluoro-3,5-dihalopyridyloxy compounds as set forth hereinabove.

An outstanding feature of the present invention is the ability of the presently claimed compounds to control, either by post-emergent or pre-emergent application, the growth of grasses and broadleaf plants, such as, for example, barnyard grass, crabgrass, yellow foxtail, Johnson grass, wild oats, bindweed, pigweed, ragweed, wild mustard, beans, cotton, sorghum, corn, rice, soybeans and wheat.

The application of the compounds of the present invention to plants and plant parts and their habitats, gives rise to varying degrees of response to the compounds depending upon the nature of the plant or seed, the stage of growth or maturity of the plant, the specific compound employed, and the dosage at which plant or plant part or habitat exposure to the compound is carried out, as well as environmental conditions. When large dosages of many of the compounds are applied to the foliage of undesirable plants, a substantially complete kill is obtained. Soil or foliar applications of more dilute dosages of many of the compounds suppress the growth of the germinant seeds and seedlings of many undesirable grasses while having little or no effect upon the seeds, emerging seedlings or established plants of many desirable crop plants. Thus, many of the compounds can be employed for the selective control of emerging seedlings of undesirable weeds in plantings or stands of desirable crop plants.

The minimum amount of active compound applied should be that which is effective in controlling and/or killing undesirable plant growth. Ordinarily, for pre-emergent control, good results are obtained when from 0.06 to 4 pounds or more of at least one of the active pyridyloxy compounds are applied per acre. In foliage treatment, good results are obtained when from 0.02 to 4 pounds of active compound per acre are employed. In selective applications to foliage for the control of many undesirable weeds in the presence of desired crop plants, a uniform dosage of from about 0.02 to 2 pounds of active compound can be employed. In all selective applications, the exact dosage to be employed is dependent upon the resistance of the crop plant or their seeds to the active compounds.

The present invention can be carried out by directly employing the claimed compounds singly or in combination with each other. However, the present invention also embraces the employment of liquid, granular, encapsulated or dust compositions containing at least one of said compounds. In such usage, the compound or compounds can be modified with one or more of a plurality of chemically inert additaments or pesticidal materials including solvents or other liquid carriers, surface active dispersing agents or coarsely or finely divided inert solids. The augmented compositions are also adapted to be employed as concentrates and subsequently diluted with additional inert carrier, to produce other compositions in the form of dusts, sprays, granules, washes or drenches. In compositions where the additament is a coarsely or finely divided solid, a surface active agent or the combination of a surface active agent and a liquid additament, the added material cooperates with the active component so as to facilitate the invention. Whether the composition is employed in liquid form, as a wettable powder, or as a granular or encapsulated material, the active compound will normally be present in an amount of from about 5 to about 95 percent by weight of the total composition.

In the preparation of dust compositions, the toxicant products can be compounded with any of the finely divided solids, such as, for example, pyrophyllite, talc, chalk, gypsum, fuller's earth, bentonite, attapulgite, and the like. In such operations, the finely divided carrier is ground or mixed with the toxicant or wet with a solution of the toxicant in a volatile organic solvent. Also, such dust compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided clays, such as, for example, attapulgite, bentonite, diatomite, or the like.

Similarly, the toxicant products can be compounded with a suitable water-immiscible organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of water-immiscible solvent, emulsifying agent and water. Preferred dispersing agents which can be employed in these compositions, are oil-soluble materials including non-ionic emulsifiers such as, for example, the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable organic liquids which can be employed in the composition include, for example, petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and active compound.

In addition, other liquid compositions containing the desired amount of effective agent can be prepared by dissolving the toxicant in an organic liquid such as, for example, acetone, methylene chloride, chlorobenzene and petroleum distillates. The preferred organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point above 80° F. The proportion of the compounds of this invention employed in a suitable solvent may vary from about 2 to about 50 percent or higher.

In further embodiments, the compounds as employed in accordance with the present invention, or compositions containing the same, can be advantageously employed in the present invention in combination with one or more pesticidal or preservative compounds. In such embodiments, the pesticidal or preservative compound is employed either as a supplemental toxicant or as an additament. Representative operable pesticidal or preservative compounds include substituted phenols, cresols, substituted cresols and their metal salts, bisphenols and thiobisphenols; halogenated salicylanilides, organo sulfur compounds, carbamate compounds, quaternary ammonium compounds, organometallic compounds, inorganic salts and miscellaneous other compounds, such as phenol, cresol, trichlorophenols, tetrachlorophenols, pentachlorophenol, P-chloro-m-cresol, sodium pentachlorophenol and other sodium, potassium, etc. salts of the phenols, substituted phenols, cresols and substituted cresols, di- and tribrominated salicylanilides, 2,2'-methylenebis(3,4,6-trichlorophenol), 2,2'-thiobis(4,6-dichlorophenoxide), halogenated trifluoromethyl salicylanilide, disodium ethylenebisthiocarbamate, sodium N-methyldithiocarbamate, zinc dimethyldithiocarbamate, 2-mercaptobenzothiazole, 3,5-dimethyltetrahydro-1,3,5-2H-thioadiazine-2-thione, 2,3-dinitro-1,4-dithia-anthraquinone, dodecyl pyridinium chloride, alkyl dimethyl benzyl ammonium chloride, dialkyl dimethylammonium chloride, bis-tributyltin oxide, bis-tripropyltin oxide, copper pentachlorophenate, copper 8-hydroxyquinolate, sodium borate, 9-undecylenic acid, 10,10'-oxybisphenoxarsine, 1-(3-chloroallyl)-3,5,7-triaza-1-azonia-adamantane chloride, 1,4-bromobisacetobutene and substituted phosphorothioates (soil applied insecticides).

In application to an area to be treated, the compounds of this invention may be applied by spraying or by the use of mechanical spreaders in accordance with conventional practice. With respect to application, however, it will be noted that, depending upon the particular circumstances encountered, one method of application may be preferable over others. Thus, for example, for preferred pre-emergence application it has been found very satisfactory to apply the active compound in a liquid spray or on granules and incorporate it into the soil.

In a further method, the distribution can be accomplished by introducing a toxicant or toxicants into the water employed to irrigate the soil. In this method, the amount of water can be varied in accordance with the moisture equivalent or field capacity of the soil in order to obtain the desired depth of distribution of the toxicant.

The following embodiments are illustrative of the present methods.

EXAMPLE XV

Forty-five parts by weight of 4-(3,5-dichloro-6-fluoro-2-pyridyloxy)-1-butanol is mixed and ground with 5 parts by weight of Triton X-155 surfactant (an alkylated aryl polyether alcohol) to prepare a water-dispersible concentrate composition containing 90 percent by weight of the ester compound.

In a further operation, 25 parts by weight of methyl(3,5-dichloro-6-fluoro-2-(pyridyloxy)acetate, 10 parts by weight of Triton X-155 surfactant and 65 parts by weight of xylene are mixed together to prepare an emulsifiable concentrate composition containing 25 percent by weight of said ester compound.

A mixture of 10 parts by weight of 6-(3,5-dichloro-6-fluoro-2-pyridyloxy)-1-hexanol, 10 parts by weight of 2-[2-(3,5-dichloro-6-fluoro-2-pyridyloxy)ethoxy]ethanol, 0.1 part of Nacconol NR detergent (alkyl sulfonate), 0.1 part of Daxad No. 27 (a polymerized sodium salt of benzoid alkyl sulfonic acids) and 200 parts of water are ball-milled together to prepare a water dispersible liquid concentrate composition containing 20 parts by weight of the mixed pyridine compounds. The concentrate compositions thus prepared can be dispersed in water to prepare aqueous compositions which have very desirable wetting and penetrating properties and are adapted to distribute growth inhibiting amounts of the 6-fluoro-3,5-dihalo-2-pyridyloxy compounds on plant parts.

EXAMPLE XVI

In separate operations, aqueous compositions containing 6-fluoro-3,5-dihalopyridyloxy compounds are prepared as follows:

Four parts by weight of one of the ester compounds, 0.08 part of sorbitan trioleate (Span 85), and 0.02 part of a sorbitan monoleate polyoxyethylene derivative (Tween 80) are dispersed in 40 milliliters of acetone to produce a concentrate composition in the form of a water-soluble liquid containing one of the ester compounds as the sole active agent. The compounds employed in these procedures include the following:
  (3,5-Dichloro-6-fluoro-2-pyridyloxy) acetonitrile;
  (3,5-Dichloro-6-fluoro-2-pyridyloxy) acetic acid;
  Methyl(3,5-dichloro-6-fluoro-2-pyridyloxy) acetate;
  Ethyl(3,5-dichloro-6-fluoro-2-pyridyloxy) acetate;
  (3,5-Dibromo-6-fluoro-2-pyridyloxy) acetic acid;
  Ethyl(3,5-dibromo-6-fluoro-2-pyridyloxy) acetate;
  2-(3,5-Dichloro-6-fluoro-2-pyridyloxy)propionic acid;
  Ethyl[2-(3,5-dichloro-6-fluoro-2-pyridyloxy)]propionate;
  2-(3,5-Dichloro-6-fluoro-2-pyridyloxy)acetamide;
  2-Methoxyethyl(3,5-dichloro-6-fluoro-2-pyridyloxy)acetate;
  Ammonium(3,5-dibromo-6-fluoro-2-pyridyloxy)acetate;
  Methyl ammonium(3,5-dichloro-6-fluoro-2-pyridyloxy)-acetate;
  Butyl ammonium(3,5-dichloro-6-fluoro-2-pyridyloxy)-acetate;
  Dimethyl ammonium(3,5-dibromo-6-fluoro-2-pyridyloxy)-acetate;
  Dibutyl ammonium[2(3,5-dichloro-6-fluoro-2-pyridyloxy)]propionate;
  Diisopropanol ammonium(3,5-dichloro-6-fluoro-2-pyridyloxy)acetate;
  Tributyl ammonium(6-fluoro-3,5-diiodo-2-pyridyloxy)-acetate;
  Ethanol ammonium(3,5-dichloro-6-fluoro-2-pyridyloxy)-acetate;
  Methylethyl ammonium(3,5-dichloro-6-fluoro-2-pyridyloxy)acetate;
  Methylbutyl ammonium(3,5-dichloro-6-fluoro-2-pyridyloxy)acetate;
  Methyldiisopropanol ammonium[2(3,5-dichloro-6-fluoro-2-pyridyloxy)]propionate;
  2-n-Butoxyethyl(3,5-dichloro-6-fluoro-2-pyridyloxy)acetate;
  2-(2-Methoxyethyl(3,5-dichloro-6-fluoro-2-pyridyloxy))-propionate;
  2-(1-Methyl-2-n-butoxyethyl(3,5-dichloro-6-fluoro-2-pyridyloxy))propionate;
  2-(3,5-Dichloro-6-fluoro-2-pyridyloxy) ethyl 2,2-dichloropropionate;
  2-(3,5-Dichloro-6-fluoro-2-pyridyloxy) ethyl acetate;
  3,5-Dichloro-6-fluoro-2-(2-phenoxyethoxy)-pyridine;
  2-[2-(2-(3,5-Dichloro-6-fluoro-2-pyridyloxy)ethoxy)-ethoxy]ethanol;
  3,5-Dichloro-2-(2-ethoxyethoxy)-6-fluoropyridine;
  3,5-Dichloro-6-fluoro-2-(2-(2-methoxyethoxy)ethoxy)pyridine;
  2-(3,5-Dichloro-6-fluoro-2-pyridyloxy)ethyl N-methyl carbamate;
  2-(3,5-Dichloro-6-fluoro-2-pyridyloxy)ethyl N-phenyl carbamate;
  2-(3,5-Dichloro-6-fluoro-2-pyridyloxy)ethyl propionate
  2-[2-(2-Butoxyethoxy)ethoxy]-3,5-dichloro-6-fluoropyridine;
  2-(3,5-Dichloro-6-fluoro-2-pyridyloxy) ethyl 2,2-dimethylpropionate;
  3,5-Dichloro-6-fluoro-2-(2-phenoxyethoxy)pyridine;
  2-(2-Butoxyethoxy)-3,5-dichloro-6-fluoropyridine;
  3,5-Dichloro-6-fluoro-2-(2-methoxyethoxy)pyridine;
  2-(3,5-Dichloro-6-fluoro-2-pyridyloxy) ethyl 2-methylpropionate;
  3,5-Dichloro-6-fluoro-2-(2-(2-ethoxyethoxy)ethoxy)-pyridine;
  3,5-Dichloro-6-fluoro-2-(2-methoxy-1-methylethoxy)-pyridine;
  2-(3,5-Dichloro-6-fluoro-2-pyridyloxy) N-methyl acetamide;
  2-(3,5-Dichloro-6-fluoro-2-pyridyloxy) N-butyl acetamide;
  2-(3,5-Dichloro-6-fluoro-2-pyridyloxy) N-octyl acetamide;
  2-(3,5-Dichloro-6-fluoro-2-pyridyloxy) N-(2-hydroxyethyl)-N-methyl acetamide;
  N-[(3,5-Dichloro-6-fluoro-2-pyridyloxy)acetyl]-glycine;
  2-(3,5-Dichloro-6-fluoro-2-pyridyloxy) N-(2-hydroxy ethyl)acetamide;

2-(3,5-Dichloro-6-fluoro-2-pyridyloxy)ethanol;
Mixture of 2-(3,5-Dichloro-6-fluoro-2-pyridyloxy)-1-propanol and 1-(3,5-dichloro-6-fluoro-2-pyridyloxy)-2-propanol;
4-(3,5-Dichloro-6-fluoro-2-pyridyloxy)-1-butanol;
4-(3,5-Dichloro-6-fluoro-2-pyridyloxy)-2-buten-1-ol;
2-[2-(3,5-Dichloro-6-fluoro-2-pyridyloxy)ethoxy]ethanol;
6-(3,5-Dichloro-6-fluoro-2-pyridyloxy)-1-hexanol and
3-(3,5-Dichloro-6-fluoro-2-pyridyloxy)-1,2-propanediol.

Portions of these concentrate compositions are dispersed in separate portions of water to provide aqueous compositions, each containing 0.44 pound of one of the pyridyloxy compounds per 100 gallons of ultimate aqueous mixture. The diluted compositions have very desirable wetting and penetrating properties and are adapted to distribute growth inhibiting amounts of the compound on plant parts.

EXAMPLE XVII

Representative products of the present invention were evaluated for the post-emergent control of barnyard grass, wild mustard, crabgrass, pigweed, yellow foxtail and bindweed. In these evaluations, plots of the above plant species grown to a height of about 4 inches were used. Aqueous spray compositions, each containing 4,000 parts of a given 6-fluoro-3,5-dihalopyridyloxy compound per million parts of ultimate composition, were prepared in accordance with the procedures of Example XVI, and each separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated. The results of the examination of the treated plots are set forth below in Table A.

Table A

| Compound Employed | Percent Kill and Control of | | | | | |
|---|---|---|---|---|---|---|
| | Barnyard Grass | Wild Mustard | Crabgrass | Pigweed | Yellow Foxtail | Bindweed |
| N-[(3,5-Dichloro-6-fluoro-2-pyridyloxy)-acetyl]glycine | 100 | 100 | 90 | 100 | 95 | 100 |
| 2-(3,5-Dichloro-6-fluoro-2-pyridyloxy)-N-(2-hydroxyethyl)acetamide | 100 | 100 | 90 | 100 | 90 | 100 |
| Methyl(3,5-dichloro-6-fluoro-2-pyridyloxy)acetate | 100 | N.R.[1] | 80 | 100 | 100 | 100 |
| (3,5-Dichloro-6-fluoro-2-pyridyloxy) acetamide | 50 | 90 | 85 | 100 | 100 | 100 |
| (3,5-Dichloro-6-fluoro-2-pyridyloxy) acetic acid | 100 | 85 | 90 | 100 | 95 | 100 |
| 2-(3,5-Dichloro-6-fluoro-2-pyridyloxy)-ethanol | 100 | 100 | 100 | 100 | 100 | 100 |
| (3,5-Dichloro-6-fluoro-2-pyridyloxy) acetonitrile | 90 | 90 | 90 | 100 | 90 | 100 |
| 2-[2-(3,5-Dichloro-6-fluoro-2-pyridyloxy)-ethoxy]ethanol | 80 | 60 | 80 | 100 | 70 | 90 |
| 6-(3,5-Dichloro-6-fluoro-2-pyridyloxy)-1-hexanol | 100 | 100 | 95 | 100 | 90 | 100 |
| 2-(3,5-Dichloro-6-fluoro-2-pyridyloxy)-N-methyl-acetamide | 90 | 100 | 90 | 100 | 100 | 100 |
| 2-(3,5-Dichloro-6-fluoro-2-pyridyl oxy) ethyl acetate | 90 | N.R.[1] | 80 | 100 | 80 | N.R.[1] |
| 2-(3,5-Dichloro-6-fluoro-2-pyridyloxy) ethyl-N-methyl carbamate | 80 | N.R.[1] | 80 | 100 | 80 | N.R.[1] |
| 2-(3,5-Dichloro-6-fluoro-2-pyridyloxy)-ethyl propionate | 95 | N.R.[1] | 90 | 100 | 90 | N.R.[1] |
| 2-(3,5-Dichloro-6-fluoro-2-pyridyloxy)-ethyl-N-phenyl carbamate | 80 | N.R.[1] | 80 | 100 | 80 | N.R.[1] |
| 2-(3,5-Dichloro-6-fluoro-2-pyridyloxy)-ethyl 2,2-dimethylpropionate | 95 | N.R.[1] | 50 | 100 | 60 | N.R.[1] |
| 2-[2-(2-Butoxyethoxy)ethoxy]-3,5-dichloro-6-fluoropyridine | 60 | N.R.[1] | 70 | 80 | 40 | N.R.[1] |
| 3,5-Dichloro-6-fluoro-2-(2-methoxyethoxy)-pyridine | 20 | N.R.[1] | 70 | 60 | 70 | N.R.[1] |
| 3,5-Dichloro-2-6-fluoro-(2-ethoxyethoxy)-pyridine | 40 | N.R.[1] | 80 | 70 | 90 | N.R.[1] |
| 3,5-Dichloro-6-fluoro-2-(2-methoxy-1-methylethoxy)pyridine | 70 | N.R.[1] | 60 | 100 | 60 | N.R.[1] |
| Control | 0 | 0 | 0 | 0 | 0 | 0 |

[1] N.R. = Not run

EXAMPLE XVIII

Additional products of the present invention were evaluated for the post-emergent control of barnyard grass, wild mustard, crabgrass, pigweed, yellow foxtail and bindweed. In these evaluations, plots of the above plant species grown to a height of about 4 inches were used. Aqueous spray compositions, each containing 3,000 parts of a given 6-fluoro-3,5-dihalopyridyloxy compound per million parts of ultimate composition, were prepared in accordance with the procedures of Example XVI, and each separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated. The results of the examination of the treated plots are set forth below in Table B.

above plant species were treated with like compositions containing no toxicant to serve as control plots. The treating applications were carried out by drenching the

TABLE B

| | Percent Kill and Control of | | | | | |
|---|---|---|---|---|---|---|
| Compound Employed | Barnyard Grass | Wild Mustard | Crab-grass | Pig-weed | Yellow Foxtail | Bind-weed |
| 2-(3,5-Dichloro-6-fluoro-2-pyridyloxy)-propionic acid | 90 | 95 | 90 | 80 | 90 | N.R.[1] |
| (3,5-Dibromo-6-fluoro-2-pyridyloxy) acetic acid | 90 | 85 | 85 | 80 | 70 | 80 |
| Ethyl(3,5-dibromo-6-fluoro-2-pyridyloxy)acetate | 85 | 85 | 80 | 70 | 60 | 95 |
| Control | 0 | 0 | 0 | 0 | 0 | 0 |

[1]N.R. = Not run

EXAMPLE XIV

Aqueous compositions of various ester compounds prepared in accordance with Example XVI were employed for pre-emergent applications on plots immediately after they were seeded with crabgrass, wild oats, barnyard grass, wild mustard, pigweed, yellow foxtail and bindweed. Other plots similarly seeded with the soil with the aqueous compositions to obtain a treating rate of 2.0 pounds per acre. Thereafter, the plots were maintained under conditions conducive for good plant growth. Two weeks after treatment, the plots were examined to determine the percent plant growth and evaluated. The results of the examinations are set forth below in Table C.

TABLE C

| | Percent Kill and Control of | | | | | | | | |
|---|---|---|---|---|---|---|---|---|---|
| Compound Employed | Johnson Grass | Barnyard Grass | Wild Mustard | Crab-grass | Pig-weed | Yellow Foxtail | Bind-weed | Wild Oats | Rag-weed |
| 2-(3,5-Dichloro-6-fluoro-2-pyridyloxy)-propionic acid | 90 | 90 | 100[1] | 100[2] | NR[3] | 75 | 100[2] | 50 | 70 |
| 2-(3,5-Dichloro-6-fluoro-2-pyridyloxy)-N-methyl acetamide | 100 | 90 | 90 | 95 | 90 | 100 | 100 | 50 | 100 |
| 6-(3,5-Dichloro-6-fluoro-2-pyridyloxy)-1-hexanol | 90 | 85[2] | 100 | 90[1] | 50[2] | 90 | 80 | 90[4] | 100 |
| 2-[2-(3,5-Dichloro-6-fluoro-2-pyridyloxy)ethoxy]ethanol | 80 | 100[2] | 100[1] | 100[2] | 100[4] | 70 | 100[4] | 50 | 100[2] |
| 2-(3,5-Dichloro-6-fluoro-2-pyridyloxy)-ethanol | 100 | 100 | 100 | 100 | 100 | 100 | 100 | 70 | 100 |
| (3,5-Dichloro-6-fluoro-2-pyridyloxy) acetic acid | 100 | 90 | 100 | 100 | 100 | 100 | 100 | — | 100 |
| 2-(3,5-Dichloro-6-fluoro-2-pyridyloxy)-acetamide | 95 | 95 | 100 | 100 | NR[3] | 85 | 100 | 75 | 100 |
| Methyl(3,5-dichloro-6-fluoro-2-pyridyloxy)acetate | 100 | 100 | NR[3] | 100 | 100 | 100[5] | 100 | 70 | NR[3] |
| 2-(3,5-Dichloro-6-fluoro-2-pyridyloxy)-N-(2-hydroxyethyl)acetamide | 90 | 95 | 100[1] | 100[2] | 100[4] | 100 | 100 | 90[4] | 100[1] |
| N-[(3,5-Dichloro-6-fluoro-2-pyridyloxy)-acetyl]glycine | 100 | 90 | 100[1] | 100[1] | 100[1] | 100[1] | 100[1] | — | 100[1] |
| 2-(3,5-Dichloro-6-fluoro-2-pyridyloxy)-N-(2-hydroxyethyl)-N-methyl acetamide | 100 | 90 | 100 | 100 | 100 | 90 | 90 | 65 | 100[2] |
| 2-(3,5-Dichloro-6-fluoro-2-pyridyloxy)-2-propanol in admixture with 3,5-Dichloro-6-fluoro-2-pyridyloxy-2-propanol | 80 | 70 | 90 | 85 | 100 | 90[4] | 100[4] | 50[5] | 100[5] |
| 3,5-Dichloro-6-fluoro-2(2-(2-methoxyethoxy)ethoxy)pyridine | 70 | 70 | N.R.[3] | 100 | N.R.[3] | 70 | N.R.[3] | N.R.[3] | N.R.[3] |
| 3,5-Dichloro-6-fluoro-2-(2-(2-ethoxyethoxy)ethoxy)pyridine | 70 | 70 | N.R.[3] | 100 | N.R.[3] | 70 | N.R.[3] | N.R.[3] | N.R.[3] |
| 2-[2-(2-(3,5-Dichloro-6-fluoro-2-pyridyloxy)ethoxy)ethoxy]ethanol | 40 | 50 | N.R.[3] | 70 | N.R.[3] | 70 | N.R.[3] | N.R.[3] | N.R.[3] |
| Ethyl[2-(3,5-dichloro-6-fluoro-2-pyridyloxy)]acetate | 99 | 90 | N.R.[3] | 100 | N.R.[3] | 90 | N.R.[3] | N.R.[3] | N.R.[3] |
| 3,5-Dichloro-6-fluoro-2-(2-ethoxyethoxy)pyridine | 70 | 50 | N.R.[3] | 70 | N.R.[3] | 70 | N.R.[3] | N.R.[3] | N.R.[3] |
| 2-(3,5-Dichloro-6-fluoro-2-pyridyloxy)ethyl N-phenyl carbamate | 90 | 80 | N.R.[3] | 100 | N.R.[3] | 80 | N.R.[3] | N.R.[3] | N.R.[3] |
| 2-(3,5-Dichloro-6-fluoro-2-pyridyloxy) ethyl 2-methylpropionate | 90 | 95 | N.R.[3] | 100 | N.R.[3] | 95 | N.R.[3] | N.R.[3] | N.R.[3] |
| 2-(3,5-dichloro-6-fluoro-2-pyridyloxy)]propionate | 100 | 95 | N.R.[3] | 100 | N.R.[3] | 95 | N.R.[3] | N.R.[3] | N.R.[3] |
| 2-(3,5-Dichloro-6-fluoro-2-pyridyloxy)ethyl-N-methyl carbamate | 80 | 80 | N.R.[3] | 100 | N.R.[3] | 80 | N.R.[3] | N.R.[3] | N.R.[3] |
| Control | 0 | 0 | 0 | 0 | 0 | 0 | 0 | 0 | 0 |

[1]Actual treating rate 0.5 pound per acre
[2]Actual treating rate 1.0 pound per acre
[3]N.R. = not run
[4]Actual treating rate 20.0 pounds per acre
[5]Actual treating rate 10.0 pounds per acre

EXAMPLE XX

Aqueous compositions of various compounds prepared in accordance with Example XVI were employed for pre-emergent applications on plots immediately prior to their being seeded with seeds of barnyard grass, pigweed and bindweed. Other plots similarly to be seeded with the above plant species were treated with the like compositions containing no toxicant to serve as control plots. The treating applications were carried out by drenching the soil with the aqueous compositions to a depth of about one inch to obtain a treating rate of 10 pounds per acre. The plots were thereafter seeded with seeds of the above plant species and the seeds covered with a sand cap and watered with sufficient water to insure seed germination. Thereafter, the plots were maintained under conditions conducive for good plant growth. Four weeks after treatment, the plots were examined to determine the percent plant growth and evaluated. The results of the examinations are set forth below in Table D.

TABLE D

| Compound Employed | Percent Kill and Control of | | |
|---|---|---|---|
| | Pigweed | Barnyard Grass | Bindweed |
| Ethyl(3,5-dibromo-6-fluoro-2-pyridyloxy) acetate | 100 | 98 | 100 |
| Ethyl[2-(3,5-dichloro-6-fluoro-2-pyridyloxy)]propionate | 100 | 90 | 100 |
| 3-(3,5-Dichloro-6-fluoro-2-pyridyloxy)-1,2-propanediol | 98 | 95 | 98 |
| 3,5-Dichloro-6-fluoro-2-(2-(2-methoxy)ethoxy)pyridine | 100 | 80 | N.R.[1] |
| 3,5-Dichloro-6-fluoro-2-(2-(2-ethoxyethoxy)ethoxy)pyridine | 100 | 70 | N.R.[1] |
| Ethyl[2-(3,5-dichloro-6-fluoro-2-pyridyloxy)]acetate | 100 | 100 | N.R.[1] |
| 2-(3,5-Dichloro-6-fluoro-2-pyridyloxy) ethyl 2,2-dichloropropionate | 100 | 99 | N.R.[1] |
| 3,5-Dichloro-6-fluoro-2-(2-phenoxyethoxy)pyridine | N.R.[1] | 70 | N.R.[1] |
| 2-(2-(2-Butoxyethoxy)ethoxy)-3,5-dichloro-6-fluoropyridine | 100 | 80 | N.R.[1] |
| 3,5-Dichloro-6-fluoro-2-(2-methoxyethoxy)pyridine | N.R.[1] | 80 | N.R.[1] |
| Ethyl[2-(3,5-dichloro-6-fluoro-2-pyridyloxy)]propionate | 100 | 99 | N.R.[1] |
| 3,5-DIchloro-6-fluoro-2-(2-ethoxyethoxy)pyridine | 100 | 80 | N.R.[1] |
| 3,5-Dichloro-6-fluoro-2-(2-methoxy-2-methylethoxy)pyridine | 100 | 70 | N.R.[1] |
| 2-(3,5-Dichloro-6-fluoro-2-pyridyloxy)ethyl-N-methyl carbamate | 100 | 80 | N.R.[1] |
| 2-(2-Butoxyethoxy)-3,5-dichloro-5-fluoropyridine | N.R.[1] | 80 | N.R.[1] |
| 2-(3,5-dichloro-6-fluoro-2-pyridyloxy) ethyl 2,2-dimethyl propionate | 100 | 90 | N.R.[1] |
| 2-(2-(2-(3,5-Dichloro-6-fluoro-2-pyridyloxy)-ethoxy)ethoxy)ethanol | 90 | 70 | N.R.[1] |
| 2-(3,5-Dichloro-6-fluoro-2-pyridyloxy)ethyl-N-phenyl carbamate | 100 | 80 | N.R.[1] |
| 3,5-Dibromo-6-fluoro-2-pyridyloxy acetic acid | 100 | 98 | 100 |
| 2-(3,5-Dichloro-6-fluoro-2-pyridyloxy)-N-butyl acetamide | 100 | 98 | 100 |
| 2-(3,5-Dichloro-6-fluoro-2-pyridyloxy)-N-octyl acetamide | 100 | 98 | 100 |
| (3,5-Dichloro-6-fluoro-2-pyridyloxy)acetonitrile | 100 | 100 | 100 |
| 4-(3,5-Dichloro-6-fluoro-2-pyridyloxy)-2-buten-1-ol | 100 | 100 | 100 |
| 4-(3,5-Dichloro-6-fluoro-2-pyridyloxy)-1-butanol | 100 | 100 | 100 |
| Control | 0 | 0 | 0 |

[1]N.R. = not run

EXAMPLE XXI

Preparation of Starting Materials
3,5-Dichloro-2,6-difluoro pyridine

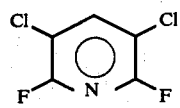

A solution was prepared by adding 20 grams (0.092 mole) of 2,3,5,6-tetrachloro pyridine and 16 grams (0.092 mole) of dried potassium fluoride to 40 milliliters of dimethylformamide. The mixture was refluxed at the reflux temperature of the mixture for 6½ hours. The reaction mixture was poured into an equal amount of water with agitation. A dark precipitate formed which was separated and extracted with hexane. The hexane layer was separated and passed through activated charcoal and filtered through diatomaceous earth. The hexane was removed by aspiration leaving 16.9 grams (92 percent yield) of the 3,5-dichloro-2,6-difluoro pyridine product. Infrared analysis of the product confirmed the structure.

EXAMPLE XXII

6-Fluoro-3,5-dichloro-2-pyridinol

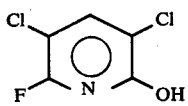

To a 500 milliliter nickel lined reaction bomb was added 10 grams (0.05 mole) of 3,5-dichloro-2,6-difluoropyridine (prepared as above, Example I), 4.4 grams (0.11 mole) of sodium hydroxide and 65 milliliters of water. The bomb was sealed and the reaction carried out at 125° C. for 2½ hours. At the completion of the reaction, the bomb was opened and the contents, which consisted of a crystalline meterial and a dark liquid, were removed. The mixture was heated until the crystals went into solution. Activated charcoal was added and the mixture filtered through diatomaceous earth. The solution was acidified, cooled and filtered to recover the crude 6-fluoro-3,5-dichloro-2-pyridinol product as a solid. The product was purified by recrystallization from hot benzene and recovered as white crystals melting at 136°–140° C. The product was recovered in a yield of 3.2 grams (31.7 percent). The structure of the product was analyzed by infrared. Upon elemental analysis, the product was found to have carbon, hydrogen, chlorine, fluorine and nitrogen contents of 33.6, 1.3, 37.2, 10.7 and 7.7 percent, respectively, as compared with the theoretical contents of 33.0, 1.1, 38.9, 10.5 and 7.7 percent, respectively, calculated for the above named compound.

EXAMPLE XXIII

6-Fluoro-3,5-dibromo-2-pyridinol

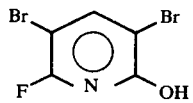

A solution was prepared by dissolving 10 grams (0.09 mole) of 6-fluoro-2-pyridinol in 50 milliliters of glacial acetic acid. A solution consisting of 28.2 grams (0.18 mole) of bromine in 10 milliliters of glacial acetic acid was added thereto with stirring over a period of 45 minutes. During the addition, the temperature was held at ~25° C. Upon the completion of the bromine addition, the mixture was stirred an additional 2 hours and allowed to stand overnight (~15 hours). The reaction mixture was poured into water and the solid which formed was removed by filtration, washed and partially dried. The crude 6-fluoro-3,5-dibromo-2-pyridinol was purified by recrystallization from hot benzene. The product was in the form of light yellow crystals melting at 175°–176° C. and was recovered in a yield of 16 grams (67 percent). Upon analysis, the product was found to have carbon, hydrogen, bromine and nitrogen contents of 22.8, 0.9, 58.7 and 5.1 percent, respectively, as compared with the theoretical contents of 22.2, 0.7, 59.0 and 5.2 percent, respectively, calculated for the above named compound.

What is claimed:

1. A compound corresponding to the formula

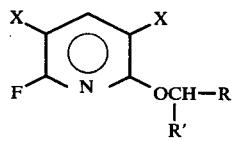

wherein X represents chloro, bromo or iodo; R' represents hydrogen or methyl and R represents alkanoyloxymethyl (—CH$_2$OCOR$^2$ wherein R$^2$ represents alkyl of 1 to 4 carbon atoms); (2,2-dichloropropionyloxy)methyl (—CH$_2$OCOC(Cl)$_2$CH$_3$); alkoxymethyl (—CH$_2$OR$^2$); phenoxymethyl (—CH$_2$O$\phi$); (2-alkoxyethoxy) methyl (—CH$_2$OCH$_2$CH$_2$OR$^2$); hydroxyalkyl (—R$^3$OH wherein R$^3$ represents alkylene of from 1 to 6 carbon atoms); 3-hydroxy-1-propenyl (—CH=CHCH$_2$OH); 1,2-dihydroxyethyl

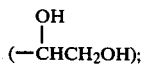

1-(2-hydroxy-ethoxy)methyl (—CH$_2$—O—CH$_2$CH$_2$OH); (2-(2-hydroxyethoxy)-ethoxy)methyl (—CH$_2$OCH$_2$CH$_2$OCH$_2$CH$_2$OH); carbamoyl (—CONR$^4$R$^4$ wherein each R$^4$ independently represents hydrogen or alkyl of 1 to 8 carbon atoms); (carboxymethyl)carbamoyl (—CONHCH$_2$COOH) or (2-hydroxyethyl)carbamoyl (—CONR$^4$CH$_2$CH$_2$OH) or (carbamoyloxy)-methyl —CH$_2$OCONHR$^5$ wherein R$^5$ is alkyl of 1 to 4 carbon atoms or phenyl).

2. The compound as defined in claim 1 wherein R is hydroxy alkyl (—R$^3$OH).

3. The compound as defined in claim 1 wherein R is 3-hydroxy-1-propenyl.

4. The compound as defined in claim 1 wherein R is 1,2-dihydroxyethyl

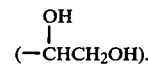

5. The compound as defined in claim 1 wherein R is 1-(2-hydroxyethoxy)methyl (—CH$_2$OCH$_2$CH$_2$OH).

6. The compound as defined in claim 1 wherein R is carbamoyl.

7. The compound as defined in claim 1 wherein R is (carboxymethyl)carbamoyl (—CONHCH$_2$COOH).

8. The compound as defined in claim 1 wherein R is (2-hydroxyethyl)carbamoyl (—CONR$^4$CH$_2$CH$_2$OH).

9. The compound as defined in claim 1 wherein R is loweralkanoyloxymethyl (—CH$_2$OCOR$^2$).

10. The compound as defined in claim 1 wherein R is (2,2-dichloropropionyloxy)methyl (—CH$_2$OCOC(Cl)$_2$CH$_3$).

11. The compound as defined in claim 1 wherein R is loweralkoxymethyl (—CH$_2$OR$^2$).

12. The compound as defined in claim 1 wherein R is phenoxymethyl (—CH$_2$O$\phi$).

13. The compound as defined in claim 1 wherein R is (2-loweralkoxyethoxy)methyl (—CH$_2$OCH$_2$CH$_2$OR$^2$).

14. The compound as defined in claim 1 wherein R is (2-(2-hydroxyethoxy)ethoxy)methyl (—CH$_2$OCH$_2$CH$_2$OCH$_2$CH$_2$OH).

15. The compound as defined in claim 1 wherein R is (carbamoyloxy)methyl (—CH$_2$OCONHR$^5$).

16. The compound as defined in claim 2 which is 2-(3,5-dichloro-6-fluoro-2-pyridyloxy)ethanol.

17. The compound as defined in claim 2 which is 4-(3,5-dichloro-6-fluoro-2-pyridyloxy)-1-butanol.

18. The compound as defined in claim 2 which is a mixture of 2-(3,5-dichloro-6-fluoro-2-pyridyloxy)-1-propanol and 1-(3,5-dichloro-6-fluoro-2-pyridyloxy)-2-propanol.

19. The compound as defined in claim 9 which is 2-(3,5-dichloro-6-fluoro-2-pyridyloxy) ethyl acetate.

20. The compound as defined in claim 9 which is 2-(3,5-dichloro-6-fluoro-2-pyridyloxy) ethyl propionate.

21. The compound as defined in claim 9 which is 2-(3,5-dichloro-6-fluoro-2-pyridyloxy) ethyl 2-methyl propionate.

22. The compound as defined in claim 12 which is 3,5-dichloro-6-fluoro-2-(2-phenoxyethoxy)pyridine.

23. The compound as defined in claim 13 which is 3,5-dichloro-6-fluoro-2-(2-(2-methoxyethoxy)ethoxy)-pyridine.

24. The compound as defined in claim 14 which is 2-[2-(3,5-dichloro-6-fluoro-2-pyridyloxy)ethoxy]ethanol.

25. The compound as defined in claim 15 which is 2-(3,5-dichloro-6-fluoro-2-pyridyloxy) ethyl N-methylcarbamate.

26. A composition for the control of undesirable plant growth which comprises as the active agent, a compound corresponding to the formula

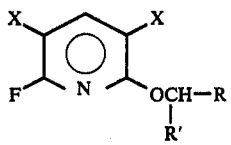

wherein X represents chloro, bromo or iodo; R' represents hydrogen or methyl and R represents alkanoyloxymethyl (—CH$_2$OCOR$^2$ wherein R$^2$ represents alkyl of 1 to 4 carbon atoms); (2,2-dichloropropionyloxy)methyl (—CH$_2$OCOC(Cl)$_2$CH$_3$); alkoxymethyl (—CH$_2$OR$^2$); phenoxymethyl (—CH$_2$O$\phi$); (2-alkoxyethoxy)—methyl (—CH$_2$OCH$_2$CH$_2$OR$^2$); hydroxyalkyl (—R$^3$OH wherein R$^3$ represents alkylene of from 1 to 6 carbon atoms); 3-hydroxy-1-propenyl (—CH=CHCH$_2$OH); 1,2-dihydroxyethyl

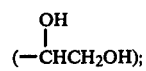

1-(2-hydroxyethoxy)methyl (—CH$_2$—O—CH$_2$CH$_2$OH); (2-(2-hydroxyethoxy)ethoxy)methyl (—CH$_2$OCH$_2$CH$_2$OCH$_2$CH$_2$OH); carbamoyl (—CONR$^4$R$^4$ wherein each R$^4$ independently represents hydrogen or alkyl of 1 to 8 carbon atoms); (carboxymethyl)carbamoyl (—CONHCH$_2$COOH) or (2-hydroxyethyl)carbamoyl (—CONR$^4$CH$_2$CH$_2$OH) or (carbamoyloxy)methyl (—CH$_2$OCONHR$^5$ wherein R$^5$ is alkyl of 1 to 4 carbon atoms or phenyl) in admixture with an inert carrier therefor.

27. The composition of claim 26 wherein the active agent constitutes from about 5 to about 95 percent by weight of the total composition.

28. The composition as defined in claim 26 wherein the active compound is 4-(3,5-dichloro-6-fluoro-2-pyridyloxy)-1-butanol.

29. The composition as defined in claim 26 wherein the active compound is 2-(3,5-dichloro-6-fluoro-2-pyridyloxy)ethyl acetate.

30. The composition as defined in claim 26 wherein the active compound is 2-(3,5-dichloro-6-fluoro-2-pyridyloxy)ethyl propionate.

31. The composition as defined in claim 26 wherein the active compound is 2-(3,5-dichloro-6-fluoro-2-pyridyloxy)ethyl 2-methyl propionate.

32. The composition as defined in claim 26 wherein the active compound is 3,5-dichloro-6-fluoro-2-(2-(2-methoxyethoxy)ethoxy)pyridine.

33. The composition as defined in claim 26 wherein the active compound is 2-[2-(3,5-dichloro-6-fluoro-2-pyridyloxy)ethoxy]ethanol.

34. The composition as defined in claim 26 wherein the active compound is 2-(3,5-dichloro-6-fluoro-2-pyridyloxy)ethyl N-methylcarbamate.

35. A method for inhibiting the growth of undesirable plant species which comprises applying to plants, plant parts or their habitats a growth-inhibiting amount of at least one compound corresponding to the formula

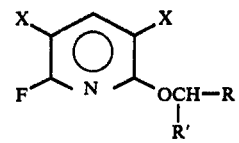

wherein X represents chloro, bromo or iodo; R' represents hydrogen or methyl and R represents alkanoyloxymethyl (—CH$_2$OCOR$^2$ wherein R$^2$ represents alkyl of 1 to 4 carbon atoms); (2,2-dichloropropionyloxy)methyl (—CH$_2$OCOC(Cl)$_2$-CH$_3$); alkoxymethyl (—CH$_2$OR$^2$); phenoxymethyl (—CH$_2$O$\phi$); (2-alkoxyethoxy)methyl (—CH$_2$OCH$_2$CH$_2$OR$^2$); hydroxyalkyl (—R$^3$OH wherein R$^3$ represents alkylene of from 1 to 6 carbon atoms); 3-hydroxy-1-propenyl (—CH=CHCH$_2$OH); 1,2-dihydroxyethyl

1-(2-hydroxyethoxy)methyl (—CH$_2$OCH$_2$CH$_2$OH); (2-(2-hydroxyethoxy)ethoxy)methyl (—CH$_2$OCH$_2$CH$_2$OCH$_2$CH$_2$OH); carbamoyl (—CONR$^4$R$^4$ wherein each R$^4$ independently represents hydrogen or alkyl of 1 to 8 carbon atoms); (carboxymethyl)carbamoyl (—CONHCH$_2$COOH) or (2-hydroxyethyl)carbamoyl (—CONR$^4$CH$_2$CH$_2$OH) or (carbamoyloxy)methyl (—CH$_2$OCONHR$^5$ wherein R$^5$ is alkyl of 1 to 4 carbon atoms or phenyl) in admixture with an inert carrier therefor.

36. The method of claim 35 wherein the compound is 2-(3,5-dichloro-6-fluoro-2-pyridyloxy)ethanol.

37. The method of claim 35 wherein the compound is 4-(3,5-dichloro-6-fluoro-2-pyridyloxy)-1-butanol.

38. The method of claim 35 wherein the compound is 2-(3,5-dichloro-6-fluoro-2-pyridyloxy)ethyl acetate.

39. The method of claim 35 wherein the compound is 2-(3,5-dichloro-6-fluoro-2-pyridyloxy)ethyl propionate.

40. The method of claim 35 wherein the compound is 2-(3,5-dichloro-6-fluoro-2-pyridyloxy)ethyl 2-methyl propionate.

41. The method of claim 35 wherein the compound is 3,5-dichloro-6-fluoro-2-(2-(2-methoxyethoxy)ethoxy)-pyridine.

42. The method of claim 35 wherein the compound is 2-[2-(3,5-dichloro-6-fluoro-2-pyridyloxy)ethoxy]ethanol.

43. The method of claim 35 wherein the compound is 2-(3,5-dichloro-6-fluoro-2-pyridyloxy)ethyl N-methylcarbamate.

* * * * *